United States Patent [19]

Cummins

[11] 4,066,072
[45] Jan. 3, 1978

[54] COMFORT CUSHION FOR INFANTS

[76] Inventor: Betty L. Cummins, Ocean Vista No. 202, 1803 E. Ocean Blvd., Long Beach, Calif. 90802

[21] Appl. No.: 657,580

[22] Filed: Feb. 12, 1976

[51] Int. Cl.² ............................................. A61H 1/00
[52] U.S. Cl. ........................................ 128/40; 5/366;
5/370; 128/2 S; 128/2.05 S
[58] Field of Search ............. 128/1 B, 1 C, 1 R, 2 K, 128/2 R, 2 S, 2.05 R, 2.05 S, 33, 38, 39, 40, 64, 376; 5/108, 109, 345 R, 348 R, 348 WB, 366, 370

[56] References Cited

U.S. PATENT DOCUMENTS

| | | | |
|---|---|---|---|
| 1,282,908 | 10/1918 | Miller | 128/2.05 S |
| 3,292,611 | 12/1966 | Belkin | 128/1 C |
| 3,419,923 | 1/1959 | Cowan | 5/109 |
| 3,595,223 | 7/1971 | Castagna | 128/33 |
| 3,658,052 | 4/1972 | Alter | 128/1 B |
| 3,760,147 | 9/1973 | Tyrey | 5/366 |

*Primary Examiner*—William E. Kamm
*Attorney, Agent, or Firm*—Charles A. Goodall

[57] ABSTRACT

A comfort cushion for infants comprising in combination a fluid filled flexible elastic hermetically sealed infant supporting mattress; a pulsating fluid pump means having mattress inlet and outlet fluid conducting conduits communicating between the pump means and the mattress for circulating a substantially non-compressible fluid through the mattress; and an infant heart beat and breathing alarm means having sensor means embedded in a mattress infant supporting surface for actuating an alarm means external to the mattress if an infant supported on the mattress were to stop breathing or its heart were to stop beating or if either breathing or heart beat were to change such as to indicate peril to the infant. The mattress inlet conduit has a pressure activated valve within the mattress which opens at a preselected fluid flow pressure and closes upon the pressure dropping below a lower pre-selected pressure to simulate sounds and fluid movement conditions a preborn infant experiences.

24 Claims, 16 Drawing Figures

U.S. Patent  Jan. 3, 1978  Sheet 1 of 3  4,066,072
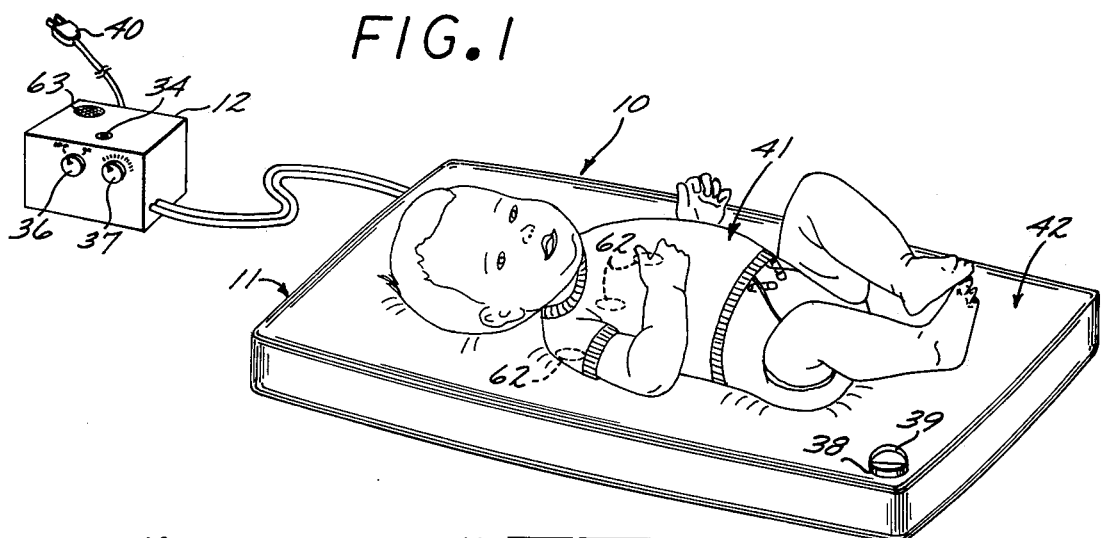
FIG. 1
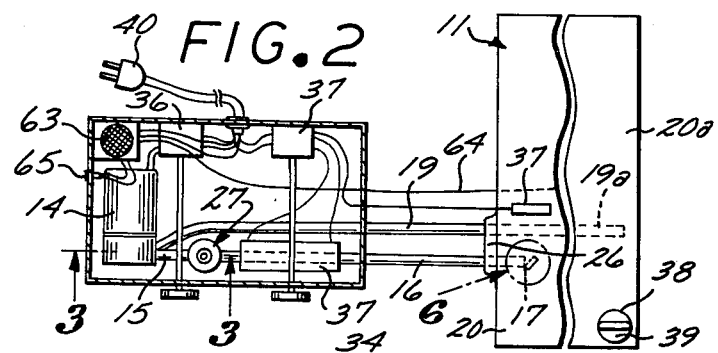
FIG. 2
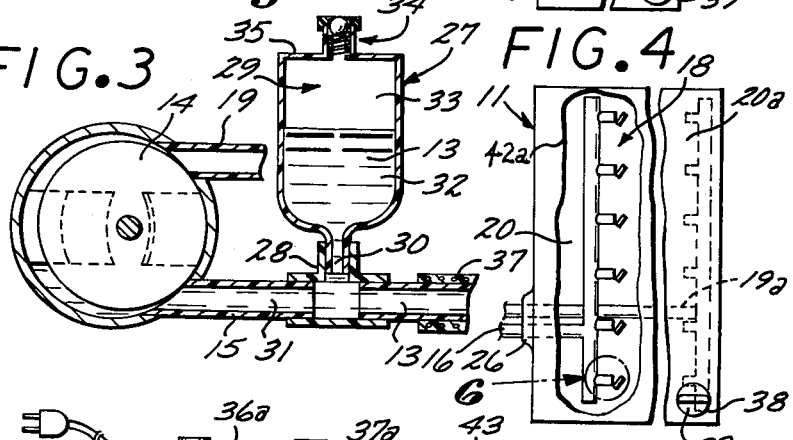
FIG. 3  FIG. 4
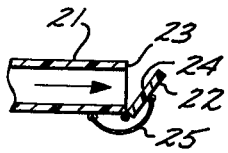
FIG. 6
FIG. 7
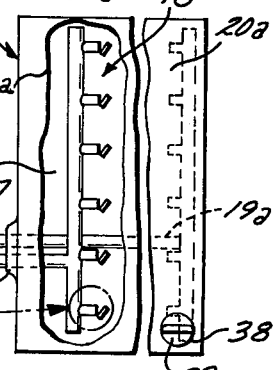
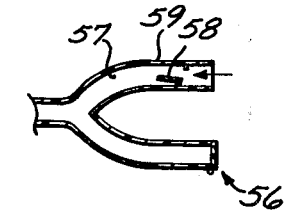
FIG. 8
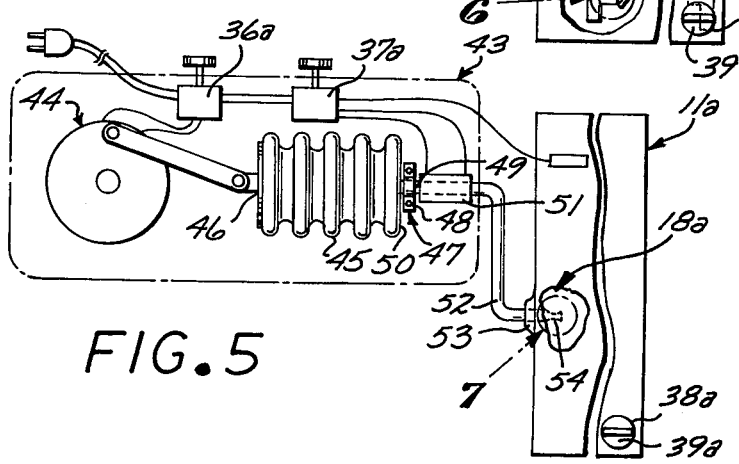
FIG. 5
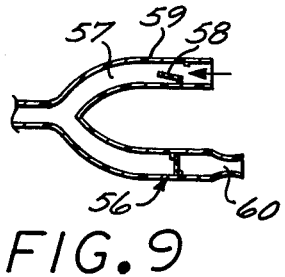
FIG. 9

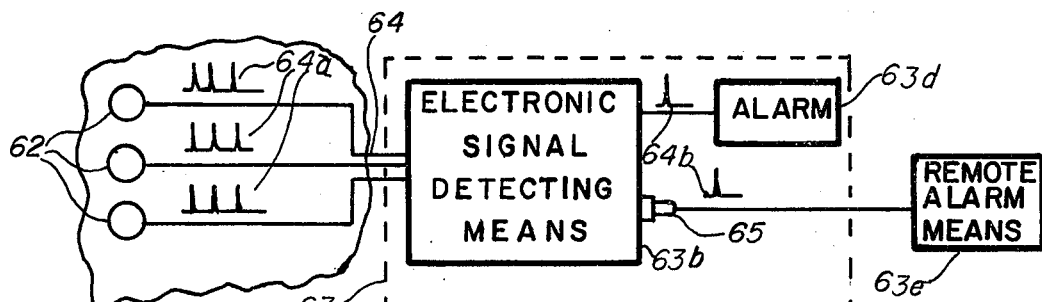
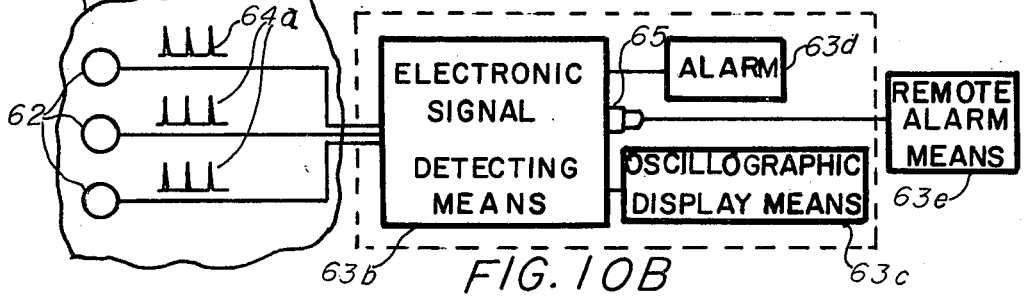
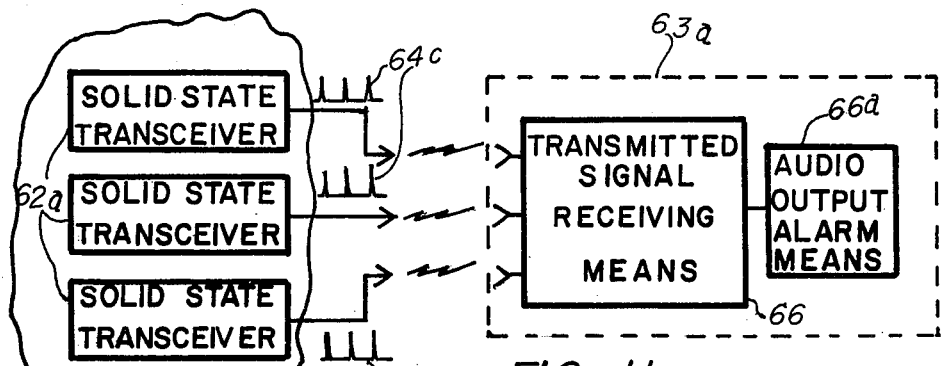
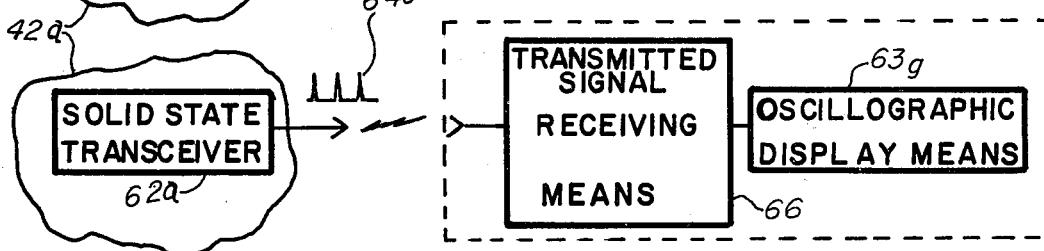
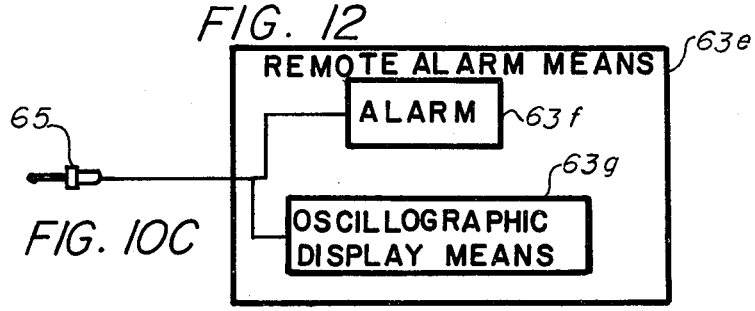

COMFORT CUSHION FOR INFANTS

BACKGROUND OF THE INVENTION

1. Field of the Invention

The present invention relates to water beds for infants and more particularly to a water bed for an infant for simulating the environmental pulsating movements and sounds an infant supported on the bed experienced prior to birth, said water bed having an infant heart beat and breathing monitoring sensor means included therewith, said sensors for actuating an external alarm if a supported infant's heart beat or breathing were to change in a manner indicating the infant were in danger.

2. Discussion of Prior Art

Vibrating water beds have been used for physiotherapeutic applications extensively. A number of methods have been employed to create vibrations in the water bed and to transfer these vibrations to a human anatomy supported on the water bed. One method employing a water-filled support cushion with vibratory impulses supplied thereto by a pulsating pump is described in U.S. Pat. No. 3,085,568 issued to H. Whitsell Apr. 16, 1963. In the Whitsell patent an external pump having inlet and outlet valves integral therewith is used to pump pulses of water into a water bed through an inlet conduit and thence out of the water bed through an outlet conduit. It should be noted that the valves are external to the water bed and hence the sounds produced by the valves opening and closing are not transmitted adequately to the water bed and hence to the human supported on the water bed. The sounds of the opening and closing valves and the pump means together with the sounds produced by the water moving in the fluid filled mattress of the present invention and the gentle motion of the mattress infant supporting surface are important in creating a feeling of kinship and security in the supported infant such as it experienced while inside the womb. The present invention provides these stimuli which are missing in the prior art. The invention also provides in combination with these stimuli a means for heating the fluid in the comfort cushion for infants so that the mother's body temperature can be simulated within the cushion and an infant heart beat and breathing sensor means for actuating an alarm means if these life functions alter in a manner indicating the supported infant is in peril.

SUMMARY OF THE INVENTION

It is an object of this invention to provide an infant comfort cushion for pulsatingly pumping a substantially non-compressible fluid into and out of a flexible elastic hermetically sealed infant supporting mattress in a manner simulating the sounds and movements a pre-born infant is subjected to.

Another object of this invention is to provide an infant comfort cushion wherein said fluid is circulated through said mattress through pressure actuated valves simulating sounds of a human heart beat upon opening and closing of said valves.

Another object of this invention is to provide an infant comfort cushion wherein said pulsating fluid is maintained with a temperature range simulating a human body temperature.

Yet another object of this invention to provide an infant support cushion for simulating pre-natal stimuli for an infant supported thereon including movements, sounds, and temperatures, together with an infant heart beat and breathing sensor means for actuating an alarm means if these life functions alter in a manner indicating that the infant is in peril.

These objects are achieved by providing an infant support cushion including in combination a fluid filled flexible elastic hermetically sealed mattress and a pulsating fluid pump means having mattress inlet and outlet fluid conducting conduits communicating between the mattress and the pump means for circulating a substantially non-compressible fluid by pumping the fluid through the conduits and through the mattress. The inlet conduit has fluid pressure actuated valve means within the mattress. These valve means open upon being forced by fluid pressure acting thereon at a preselected pressure and thereafter close at a lower preselected pressure. The sounds of the valves opening and closing are transmitted through the fluid and thence through a flexible elastic infant support wall to a supported infant and are heard by the supported infant. The movement of the fluid further creates a hissing or swishing sound which is also heard by the supported infant. The pulsed fluid also moves the flexible elastic infant support wall gently thereby simulating pre-natal movements experienced by the supported infant prior to its birth. Heart beat and breathing sensor means are embedded in the infant supporting wall for sensing peril indicating changes in the supported infant's heart beat and breathing and thereupon actuating an alarm means external to the mattress.

BRIEF DESCRIPTION OF THE APPLICATION DRAWINGS

FIG. 1 is a perspective view of the invention showing a pump means, a fluid filled flexible elastic hermetically sealed infant supporting mattress with an infant supported thereon—and heart beat-breathing sensor means and alarm.

FIG. 2 is a top plan view with a top cover removed from a pumping means enclosure.

FIG. 3 is a side plan view of a pumping means taken along line 3—3 of FIG. 2.

FIG. 4 is a top plan view of the mattress with a partial cut-away view of an infant support wall showing an inlet valved manifold.

FIG. 5 shows a schematic view of a reciprocating bellows type pump means with the controls for heating and pump speed together with a top plan view of a mattress.

FIG. 6 is a view of a pressure activated inlet valve means at inset 6.

FIG. 7 is a view of an inlet orifice at inset 7.

FIG. 8 shows valved inlet and outlet conduits within the mattress comprising an alternate embodiment to that of FIG. 7 without the inlet orifice.

FIG. 9 shows a valved inlet conduit with an inlet orifice thereon and a valved outlet conduit comprising an alternate embodiment as that shown in FIG. 7.

FIG. 12 is a block diagram of a sensor means shown in FIG. 11 replacing the audio output alarm means with an oscillographic display means.

DESCRIPTION OF PREFERRED EMBODIMENTS

Figure 10:
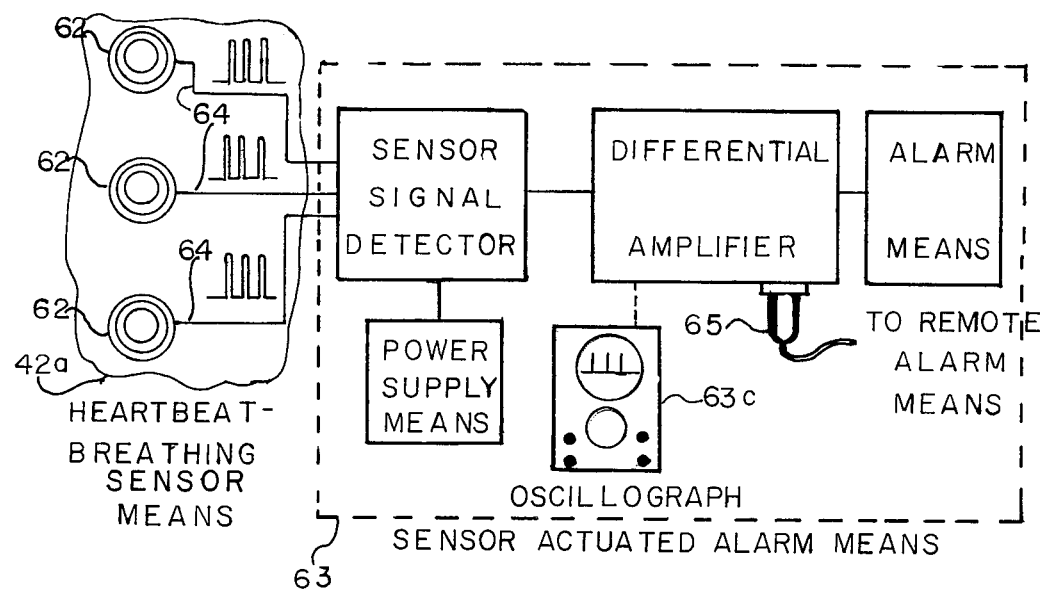
FIG. 10A shows a block diagram of a sensor means embedded in a mattress infant supporting wall in combination with a sensor actuated alarm means.
FIG. 10B is a block diagram as described in FIG. 10A further including an oscillographic display means.
FIG. 10C is a block diagram of the remote alarm means shown in FIG. 10A and FIG. 10B including a remote alarm and an oscillographic display means.
Figure 11:
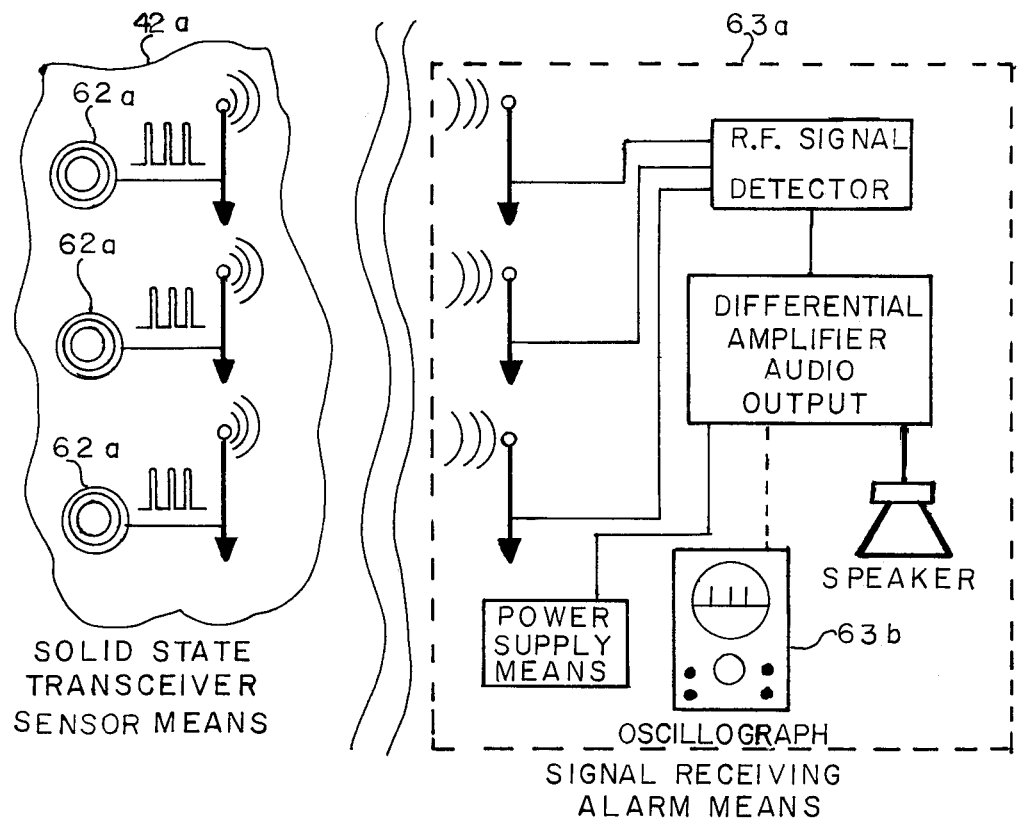
FIG. 11 shows a block diagram of a sensor means comprising a transceiver in combination with a remote sensor signal receiving alarm means.

A preferred embodiment of the comfort cushion for infants of the present invention is illustrated in the accompanying drawing and is identified generally by the reference character 10 (FIG. 1). Constructional details shown in FIGS. 2 through 9.

The illustrated embodiment of the comfort cushion for infants 10 herein comprises in combination a fluid filled flexible elastic hermetically sealed infant supporting mattress 11, a pulsating fluid pump means 12, and a heartbeat-breathing sensor means 62 and sensor actuating alarm means 63. A substantially non-compressible fluid 13 (FIG. 3) is circulated through the mattress by operation of a fluid pump 14 shown in FIGS. 2 and 3 as an electrical movable vane rotary pump. The pump means 14 pumps the fluid through a pump exhaust conduit 15 into a mattress inlet conduit 16 and thence into the mattress 11 through an inlet conduit valved opening 17. The inlet valved opening 17 is positioned within a mattress fluid chamber 18. The fluid is returned to a pump means intake conduit 19 through a mattress outlet conduit 19a which extends substantially through the mattress fluid chamber 18 and is within the chamber 18. The fluid 13 is pumped into a chamber front portion 20 and out of a chamber rear portion 20a. The inlet valved opening 17 as shown comprises a cylindrical member 21 (FIG. 6) which is integral with the inlet conduit, a pressure actuated flapper valve means 22 which closes against an inlet conduit end wall 23 and remains closed until the pumped fluid imposes sufficient force against a flapper valve front surface 24 to force it to open. The valve 22 is closed after the fluid pressure drops below a pre-selected pressure by a closing means 25, here shown as a spring means. It is understood that the valve 22 as described herein is schematic in nature and that any suitable pressure actuated valve means which may be set for a desired upper and lower pressure may be used. The inlet and outlet mattress conduits 16, 19a enter the mattress fluid chamber 18 through a hermetically sealed conduit port 26. The pump means wherein a rotary pump is used as described herein employs a pressure developing tank 27 to develop the pressure for opening and closing the inlet valve 17. The pressure tank comprises a bottle-shaped tank 27 sealably connected at a tank inlet end 28 to the pump exhaust conduit 15. A tank internal chamber 29 communicates through a narrow tank fluid inlet 30 with a conduit fluid carrying interior 31. A tank chamber lower portion 32 is partially filled with the fluid 13 as shown in FIG. 3 and a tank upper portion 33 is filled with air which is compressible. The tank has an air inlet/outlet valve 34 extending upwardly from the tank top 35 for use in venting the tank as required, particularly when filling the cushion and pump means with fluid.

A pump control rheostat means 36 is provided for regulating the speed of the variable speed pump 14 preferably within a pump speed range to produce from 20 to 100 pulses per minute for simulating a heart beat rate. A thermostatically controlled heat means 37 is provided for heating the fluid 13 and regulating the temperature of the fluid in the mattress fluid chamber 18, said heat means comprising in combination, a temperature regulator and control 37b, a thermostat 37c electrically connected to said control through electrical conducting wiring 37d, a heater 37e attached heat conductively to the inlet conduit 16 and a manual temperature control means 37f for manually setting the temperature of the heater 37c to a desired temperature, preferably with a range of temperature from 32° C. (89.6° F.) to 49° C. (120.2° F).

In operation the mattress and pumping means is filled with a non-compressible fluid such as water through a mattress fill opening 38 by removing the plug 39, filling the mattress and replacing the plug. Venting to remove all the air from the pump and mattress is facilitated by opening valve 34 on the tank 27. The pump and heat means are energized by plugging into a suitable electrical source the pump means electrical plug 40. The desired pumping speed is set on the pump speed control 36 and the desired heat is set on the heat control means 37. An infant 41 is then positioned on a mattress top surface 42 of a mattress infant supporting wall 42a (FIG. 4). The infant will then experience the gentle movement of the mattress top surface upwardly and downwardly and will hear the opening and closing of the valve 17 and the swishing and hissing noises of the water moving within the mattress and through the conduits therein thus providing an environment simulating the infant's pre-natal experiences. Further referring to FIGS. 1 and 2 an infant heartbeat-breathing sensor means 62 is embedded in a mattress infant supporting wall 42a (see FIG. 4) located generally beneath the infant's chest cavity area as shown in FIG. 1. The sensor means 62 is for detecting the infant's heart beating and breathing sounds and communicating these sounds to a sensor actuating alarm means 63 through sensor-alarm means connecting means 64 said sensor means may comprise a microphone pick-up or other similar device customarily used for detecting internal body sounds such as a stethoscope. The alarm means 63 comprises an electronic signal detecting means 63b having means for accepting a signal input 64a from the sensor proportional to the infant heart beating and breathing sounds, amplifying the signal input 64a, detecting changes in the signal input, and using the signal input changes to provide an output signal 64b to set off an alarm 63d thereby indicating changes in the supported infant's heart beats and breathing if these life functions alter in a manner indicating that the infant is in peril. The alarm means 63 is provided with an auxiliary output signal jack means 65 for connecting a remote alarm means 63e thereto. The alarm means 63 may also be provided with an oscillographic display means 63c. The remote alarm means 63e may comprise an audio alarm means 63f or a remote oscillographic display means 63g or a combination of the said alarm means 63f and display means 63g.

Referring to FIG. 1, 10A, 11, and 12, the sensor means 62 shown in FIG. 1 and FIG. 10A may further comprise one or more miniature solid state transceivers 62a (see FIG. 11 and FIG. 12) for detecting a supported infant's heart beat and breathing sounds, converting said sounds to a transmitted signal 64c proportional thereto and transmitting said signal 64c to a remote transmitted thereto and transmitting said signal 64c to a remote transmitted receiving means 66 thereafter actuating an audio output alarm means 66a or in the alternative an oscillographic display means 66b for displaying a visual signal proportional to the heart beat and/or breathing signals of the supported infant. The oscillographic display means may include an oscilloscope display or a chart display means or other visual display which falls into the general category of an oscillographic display means known and used in the art of oscillographic display.

Referring to FIG. 5 another embodiment of the invention is illustrated. This embodiment employs a reciprocating pump means 43. The pump means 43 as shown comprises a motor-driven crank means 44 operably connected through a crank arm 44a to a hollow bellows 45 at a bellows front end plate 46, said crank arm for providing reciprocating motion to the bellows front end plate 46 when the motor-driven crank means 44 rotates. The bellows 45 is clamped to a bellows mount 47 by a clamping means 48 by clamping a bellows outlet/inlet conduit 49 to the bellows mount 47. The bellows conduit 49 extends outwardly at right angles from and is sealably connected to a bellows rear endplate 50. The motor-driven crank means 44 is provided with a speed control 36a as described above with regard to FIGS. 1 and 2. A heater means 37a is provided as described above with regard to FIGS. 1 and 2. A heater 51 surrounds the bellows conduit 49 adjacent to the bellows mount 47. The bellows conduit 49 is sealably connected to a mattress fluid carying conduit 52 and the mattress conduit 52 is sealably connected to a mattress conduit port 53 and extends into the mattress chamber 18a which is enclosed by the mattress 11a. The mattress 11a is filled with a non-compressible fluid through the mattress fill port 38a and all air is excluded from the pump means and mattress during the filling procedure and thereafter the mattress fill port 38a is closed with a port plug 39a.

FIGS. 7, 8 and 9 show various embodiments of the mattress conduit fluid inlet/outlet means 54 which are within the mattress chamber 18a.

FIG. 7 shows a conduit orifice 55 having intermediate said inlet/outlet means 54 and an orifice inlet/outlet end 55a a narrowed down portion 55b said inlet/outlet end 55a being outwardly flaired to form a flaired pattern of the fluid as the fluid is pumped into the mattress chamber 18a.

FIG. 8 shows a pressure actuated bivalve means comprising an inlet conduit having an inlet pressure actuated valve 56 for permitting fluid to flow only into the chamber 18a through a fluid inlet conduit 54a when the pressure of the fluid flowing through said inlet conduit 54a reaches a first pre-determined value, said bivalve means further comprising an outlet conduit 57 sealably connected to the inlet conduit 54a intermediate the conduit port 53 and said inlet valve 56, said outlet conduit 57 extending substantially into the chamber 18a and having a one-way valve 58 at an end portion 59 for permitting fluid to flow only into said outlet conduit 57 from the chamber when the fluid pressure within said chamber reaches a second pre-determined value above that of the first fluid pressure pre-determined value.

FIG. 9 combines the features of FIGS. 7 and 8 showing an orifice 60 on the inlet conduit.

While a bellows type reciprocating pump is shown, the invention is not limited to this pump means. A piston pump would serve just as well if the pump could be made leakproof.

The operation of the comfort cushion for an infant illustrated in FIG. 5 and described herein is similar to that illustrated in FIGS. 2 and 3, except that only one conduit is required between the mattress and the pump means 43. The pump means 43 is also provided with a speed control 36a and a thermostatically controlled heater means 37a. The sensor means 62 and the sensor actuated alarm means 63 may be adapted to this embodiment also as shown in FIGS. 1 and 2.

The size of the mattress should be relatively small to assure that the supported infant will be subjected to the noise and movement environment simulating the child's pre-natal experience.

I claim as my invention:

1. A comfort cushion for infants comprising in combination:
   a fluid filled flexible elastic hermetically sealed infant supporting, elongated mattress filled with a substantially non-compressible fluid, said mattress having a fluid inlet conduit and a fluid outlet conduit sealably attached to and opening into the mattress, said inlet conduit having a pressure actuated valve means within a fluid containing chamber of the mattress for permitting said fluid to flow into the chamber only at a pre-selected fluid pressure, said mattress having a removable fill plug therein for filling and emptying said mattress with said non-compressible fluid; and
   a fluid pulsating pump means having a fluid exhaust conduit sealably connected to the said inlet conduit and a fluid intake conduit sealably connected to said outlet conduit, said pump and valve means for pulsatingly circulating said fluid into and out of said mattress in a manner simulating the sounds and movements a pre-born infant is subjected to.

2. The combination set forth in claim 1 wherein said pressure actuated valve means simulates the sounds of a human heart upon opening and closing.

3. The combination set forth in claim 1 wherein the outlet conduit extends into and substantially through said chamber.

4. The combination set forth in claim 1 wherein said inlet conduit terminates in a fluid inlet manifold within said fluid containing chamber, said manifold having a plurality of said pressure activated valve means disposed along the manifold and opening into said chamber at a pre-selected fluid pressure and closing at a lower pre-selected fluid pressure.

5. The combination set forth in claim 4 wherein said inlet manifold is transverse a mattress fluid inlet end.

6. The combination in claim 4 wherein the outlet conduit begins with a fluid outlet manifold within said chamber proximate a chamber fluid outlet end, said outlet end being oppositely disposed said inlet end and said outlet manifold being transverse said chamber fluid outlet end.

7. The combination set forth in claim 1 wherein said fluid pulsating pump means comprises in combination a variable speed movable vane rotary pump having sealably connected to the pump exhaust conduit a pulse developing pressure tank, said tank having a fluid opening end in communication with the pump exhaust conduit, said tank having a lower portion partially filled with said non-compressible fluid, said fluid in the tank being in communication with the fluid in the exhaust conduit, and said tank having an upper portion filled with air, said tank further having at a top end a valve means for venting the tank, mattress and pumping means while filling the mattress and pumping means with the non-compressible fluid, the air in the tank is compressed when the pump operates until the pre-selected pressure at which the inlet valve opens is reached, whereupon the inlet valve opens, said valve closing after the pressure drops below a lower pre-selected pressure thereby producing fluid pulsations, valve noises, and fluid movement sounds within the mattress.

8. The combination set forth in claim 7 wherein said variable speed pump is adjustable to produce any pulsation rate within the mattress within the range of from 20 to 100 pulses per minute.

9. The combination set forth in claim 1 wherein said pump means has included therewith a fluid heating means for controllably heating said non-compressible fluid.

10. The combination of claim 9 wherein said fluid heating has thermostat control means for selecting and maintaining any fluid temperature within said mattress within a range of from 32° C. (89.6° F.) to 49° C. (120.2° F.).

11. The combination set forth in claim 1 further including an infant heart beating-breathing sensor means in combination with a sensor actuated alarm means for detecting peril indicating changes in heart beats and breathing of an infant supported on the mattress.

12. The combination set forth in claim 11 wherein the sensor means comprises a plurality of two or more sensor means embedded in the infant supporting wall of the mattress having a connecting means communicating between the sensors and the alarm means.

13. The combination set forth in claim 11 wherein the sensor means comprises a microphone pickup for providing an electrical output signal proportional to sounds picked up thereby to the alarm means and wherein said alarm means detects and amplifies sound changes in heartbeat sounds produced by an infant supported on the mattress, said amplified sound changes causing an audio alarm signal to be made.

14. The combination set forth in claim 13 wherein means are provided for the audio alarm to be sounded at a remote monitoring station.

15. The combination set forth in claim 14 further providing an electrical signal output means for actuating an oscilloscope for oscillographic display of the infant's heartbeat sounds.

16. The combination set forth in claim 11 wherein the sensor means is a transceiver for receiving the infant's heartbeat sounds and transmitting said sounds to a remote sensor actuated alarm means.

17. The combination set forth in claim 16 wherein the remote alarm means provides an output signal for input to an oscilloscope for oscillographic display of the infant's heartbeat sounds.

18. A comfort cushion for infants comprising in combination:
a fluid filled flexible elastic hermetically sealed infant supporting elongated mattress filled with a substantially non-compressible fluid and having a fluid single conduit means sealably attached to an opening into the mattress at a conduit mattress connecting end, said conduit mattress connecting end opening into the mattress through a pressure actuated bivalve means, said bivalve means having a first valve means for opening an inlet conduit portion of said single conduit and permitting fluid to flow only into the mattress at a first pre-selected pressure and a second valve means for opening an outlet portion of said single conduit and permitting fluid to flow only out of the mattress at a second pre-selected pressure; and a reciprocating pump means sealably connected to said single conduit at a conduit pump connecting end oppositely disposed from said mattress connecting end, said pump means for reciprocatingly pumping said fluid into and out of said mattress through said single conduit, said mattress further having a removable fill plug means therein for filling and emptying said mattress and having a top surface for supporting an infant thereon, said bivalve means and pump means for providing movement of said supported infant and sounds in a manner for simulating the movement and sounds to which a preborn infant is subjected.

19. The combination of claim 18 wherein said inlet portion of said single conduit opens into said mattress through a sound producing orifice within the said inlet portion.

20. The combination in claim 18 wherein the reciprocating pump means comprises an hermetically sealed bellows reciprocally operated by a motor-driven crank means for reciprocally pumping said fluid through said single conduit and into and out of the mattress.

21. The combination of claim 18 wherein the reciprocating pump means is provided with a variable pump speed control means.

22. The combination of claim 21 wherein the pump speed control means comprises a means for controlling the pump speed at any speed within a pump speed range to produce pulsation movement of the matress infant supporting surface within the range of from 20 to 100 pulsations per minute.

23. The combination of claim 18 wherein the pump means is further provided with a controllable fluid heating means for setting and maintaining a fluid temperature within the mattress at a desired temperature.

24. The combination of claim 23 wherein said heating means is provided with means for controlling said fluid temperature within a range of temperature of from 32° C (89.6° F) to 49° C (120.2° F).

* * * * *